(12) United States Patent
Jay

(10) Patent No.: US 9,387,190 B2
(45) Date of Patent: Jul. 12, 2016

(54) SUSTAINED RELEASE OF TOPICAL ANESTHETICS

(71) Applicant: Michael Joseph Jay, Chapel Hill, NC (US)

(72) Inventor: Michael Joseph Jay, Chapel Hill, NC (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 14/439,535

(22) PCT Filed: Nov. 1, 2013

(86) PCT No.: PCT/US2013/068091
§ 371 (c)(1),
(2) Date: Apr. 29, 2015

(87) PCT Pub. No.: WO2014/071203
PCT Pub. Date: May 8, 2014

(65) Prior Publication Data
US 2015/0297550 A1    Oct. 22, 2015

Related U.S. Application Data

(60) Provisional application No. 61/721,567, filed on Nov. 2, 2012.

(51) Int. Cl.
| | | |
|---|---|---|
| A61K 31/216 | (2006.01) | |
| A61K 47/30 | (2006.01) | |
| A61K 47/44 | (2006.01) | |
| A61K 47/36 | (2006.01) | |
| A61K 31/245 | (2006.01) | |
| A61K 9/00 | (2006.01) | |
| A61C 7/12 | (2006.01) | |
| A61C 19/06 | (2006.01) | |
| A61C 19/08 | (2006.01) | |

(52) U.S. Cl.
CPC .............. *A61K 31/245* (2013.01); *A61C 7/125* (2013.01); *A61C 19/063* (2013.01); *A61C 19/08* (2013.01); *A61K 9/0063* (2013.01)

(58) Field of Classification Search
None
See application file for complete search history.

(56) References Cited

U.S. PATENT DOCUMENTS

| | | | |
|---|---|---|---|
| 5,192,802 | A | 3/1993 | Rencher |
| 6,074,674 | A | 6/2000 | Jay et al. |
| 6,573,282 | B1 | 6/2003 | Yaksh et al. |
| 6,589,562 | B1 | 7/2003 | Shefer et al. |
| 7,790,215 | B2 | 9/2010 | Sackler et al. |
| 2006/0099550 | A1 | 5/2006 | Faasse et al. |
| 2007/0232695 | A1 | 10/2007 | Hirsh et al. |
| 2009/0238776 | A1 | 9/2009 | Baig et al. |

FOREIGN PATENT DOCUMENTS

| | | |
|---|---|---|
| EP | 0518798 A2 | 12/1992 |
| WO | 2011/153334 A2 | 12/2011 |

OTHER PUBLICATIONS

PCT, International Preliminary Report on Patentability, PCT/US2013/068091 (issued May 5, 2015).
PCT, International Search Report, PCT/US2013/068091 (mailed Feb. 27, 2014).
"Drugs.com: Antipyrine/benzocaine/glycerin/zinc drops. Brand Name: Neotic," by Wolters Kluwer Health, Inc. (Apr. 2010).
"Relax & Wax No-Scream Cream," archive product advertising page at www.relaxnwax.com (first publication as shown, at least as early as Feb. 2011; first publication/offer of product, at least as early as May 2009).
"Treatments Pre-Waxing," archive web page at http://www.cleanandeasyspa.com/products/treatment/pre_wax/ (first publication at least as early as Jul. 2011).
de Araujo, D.R. et al., "Bioadhesive Films Containing Benzocaine: Correlation Between In Vitro Permeation and In Vivo Local Anesthetic Effect," Pharm. Res. (2010) 27:1677-1686.
Dent's Extra Strength Toothache Gum, archive product advertising page at http://www.grandpabrands.com/dent1024.html (first publication at least as early as Jan. 2004) and supplemental information.
Dhopeshwarkar, V, et al., "Evaluation of Xanthan Gum in the Preparation of Sustained Release Matrix Tablets," Drug Development and Industrial Pharmacy, 19(9), pp. 999-1017 (1993).
Hersh, E.V. et al., "Efficacy and tolerability of an intraoral benzocaine patch in the relief of spontaneous toothache pain," J. Clin, Dent., 14(1): 1-6, 2003 (abstract).
Jansson, P.E., et al., "Structure of the Extracellular Polysaccharide from *Xanthamonas campestris*," Carbohydrate Research, 45, pp. 275-282 (1975).
Kluemper, G.T. et al., "Efficacy of a wax containing benzocaine in the relief of oral mucosal pain caused by orthodontic appliances," American Journal of Orthodontics and Dentofacial Orthopedics, vol. 122, No. 4, pp. 359-365 (Oct. 2002).
Melton, L.D., et al., "Covalent Structure of the Extracellular Polysaccharide From *Xanthomonas campestris*: Evidence From Partial Hydrolysis Studes," Carbohydrate Research, 46, pp. 245-257 (1976).
Primosch, R.E. et al., "Comparison of topical EMLA 5% oral adhesive to benzocaine 20% on the pain experienced during palatal anesthetic infiltration in children," Pediatric Dentistry, 23:1, 11-13 (2001).
Reznik, D.S. et al., "Comparative Efficacy of 2 Topical Anesthetics for the Placement of Orthodontic Temporary Anchorage Devices," Anesth. Prog. (2009), 56(3): 81-85.

(Continued)

*Primary Examiner* — Yevegeny Valenrod
(74) *Attorney, Agent, or Firm* — Thompson Hine LLP

(57) ABSTRACT

A composition and method to alleviate oral mucosal discomfort and irritation in an orthodontic patient. A wax matrix containing less that 15% analgesic/anesthetic agent such as benzocaine and excipients enhanced and extended release of the analgesic/anesthetic agent compared to known art formulations. The composition exhibited desirable aesthetic properties, was easy to apply, and the relatively lower concentration of active agent provided enhanced safety.

22 Claims, 2 Drawing Sheets

(56) References Cited

OTHER PUBLICATIONS

Rosa, A.L.R. et al., "Clinical Effectiveness of Lidocaine and Benzycaine for Topical Anesthesia," Anesth. Prog., 46:97-99 (1999).

Rosivack, R.G. et al., "An Analysis of the Effectiveness of Two Topical Anesthetics," Anesth. Prog., 37:290-292 (1990).

Shin, S. et al., "Preparation and evaluation of bioadhesive benzocaine gels for enhanced local anesthetic effects," International Journal of Pharmaceuticals 260 (2003) 77-81.

Supplementary European Search Report, European Application No. 13851204.1, dated Apr. 4, 2016 (8 pages).

SUSTAINED RELEASE OF TOPICAL ANESTHETICS

This application claims priority to co-pending U.S. application Ser. No. 61/721,567 filed Nov. 2, 2012 which is expressly incorporated by reference herein in its entirety.

The discomfort and irritation of the oral mucosa that an orthodontic patient experiences during treatment is caused by friction between the oral mucosa and the orthodontic brackets. Administering painkillers or applying a commercially available non-medicated orthodontic wax over the brackets are options for orthodontic patients. However, orthodontic wax simply prevents friction and avoids further irritation, but does not reduce discomfort.

Commercially available non-medicated waxes for use in orthodontics include, e.g., GUM® Orthodontic Wax. Commercially available medicated products contain, for the most part, 20% benzocaine. "Dent's Extra Strength Toothache Gum" (Grandpa Brands, Erlanger, KY) is advertised as a medicated wax to place in an exposed tooth cavity or as a protective cover for a chipped tooth. It contains benzocaine 20%, beeswax, petrolatum, cotton, flavor, FD&C Red No. 40 Al. Lk. However, hypersensitivity reactions to beeswax have been reported, and beeswax and petrolatum are insoluble in water. There was a voluntary product recall (May 2012) due to excessive benzocaine levels in some lots.

The disclosed method and composition is an orthodontic wax matrix that provides sustained release of an analgesic/anesthetic agent, also termed "active", that is used in to alleviate oral mucosal discomfort, with the analgesic/anesthetic agent present in the matrix at a concentration that is relatively lower compared to known formulations. In one embodiment, the analgesic/anesthetic agent is benzocaine, which is the ethyl ester of para-aminobenzoic acid (PABA). In one embodiment, benzocaine is present in the matrix at a concentration from 0.1% up to less than 15%. In one embodiment, the disclosed method and composition is an orthodontic wax that contains an analgesic/anesthetic agent at a concentration lower than that previously used, and at least one excipient that provides sustained release of the analgesic/anesthetic agent from the wax matrix over at least eight hours. The composition is applied to an orthodontic bracket or brace of an orthodontic patient to relieve discomfort up to 24 hours.

DETAILED DESCRIPTION

Figure 1:
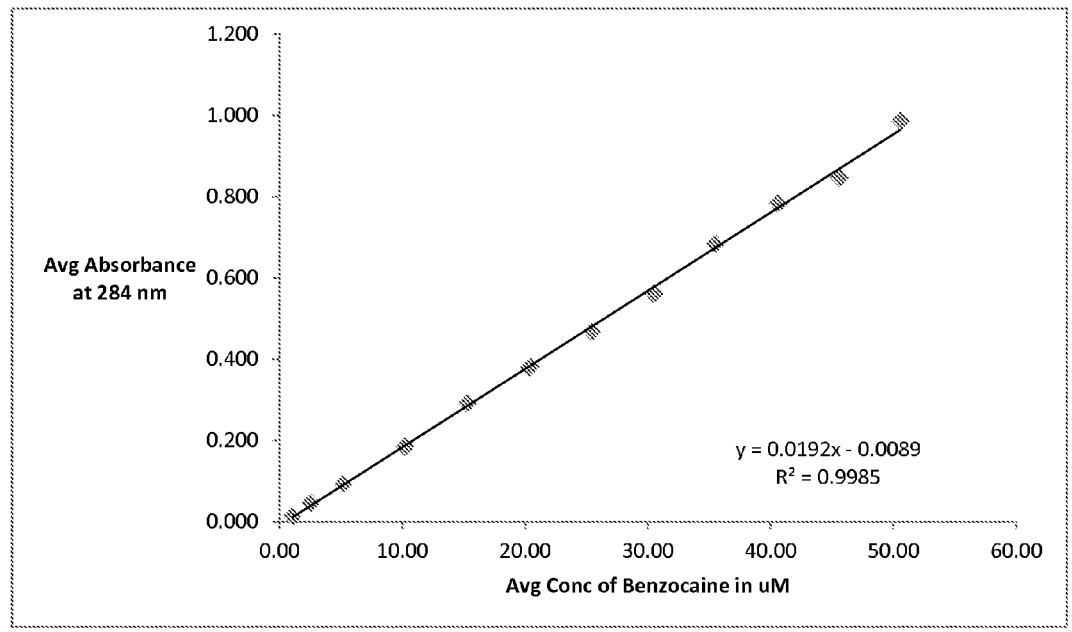
FIG. 1 illustrates a calibration curve for the optical measurement of varying concentrations of benzocaine in an artificial saliva simulant by absorbance spectroscopy at 284 nm.

As used herein, all percentage concentrations are weight/weight. As used herein, all concentration ranges are inclusive in that the upper and lower values are included within the range, and in that all sub-ranges within the range are encompassed. For example, and by way of illustration only, a range of 0%-10% concentration of a component includes the absence of that component (0%), and every concentration up to and including 10% (e.g., 0.01%-10%, 0.1%-10%, 0.2%-10%, 0.1%-9.9%, 0.1%-9.8, and so on).

In one embodiment, the formation contains xanthun gum as a sustained release agent, and benzocaine (each from Spectrum) as the analgesic/anesthetic agent. In one embodiment, this formulation additionally contains microcrystalline wax (Koster Keunen), glyceryl monosterate, heavy mineral oil, PEG 1500, and Tween 80.

Tables 1A and 1B show exemplary formulations.

TABLE 1A

| Ingredients | Weight in g | % |
|---|---|---|
| Microcrystalline wax | 21 | 83 |
| Glyceryl monosterate | 0.67 | 2.7 |
| Heavy mineral oil | 0.25 | 1.0 |
| PEG 1500 | 1.25 | 5.0 |
| Benzocaine | 1.25 | 5.0 |
| Tween 80 | 0.083 | 0.3 |
| Xanthum gum | 0.75 | 3.0 |

TABLE 1B

| Ingredients | Weight in g | % used in artificial saliva in vivo release evaluation | % Range |
|---|---|---|---|
| Microcrystalline wax | 21 | 83 | 50-99 |
| Glyceryl monosterate | 0.67 | 2.7 | 0-10 |
| Heavy mineral oil | 0.25 | 1.0 | 0-30 |
| PEG 1500 | 1.25 | 5.0 | 0-30 |
| Anesthetic/analgesic | 1.25 | 5.0 | 0.01-14.99 |
| Tween 80 (Polysorbate 80) | 0.083 | 0.3 | 0-10 |
| Xanthum gum | 0.75 | 3.0 | 0-30 |

As shown above, in embodiments, excipients are added to improve product characteristics. In general, in the above formulation of anesthetic/analgesic agent, the microcrystalline wax provides a matrix; glyceryl monostearate has known properties as an emollient, solubilizing agent, stabilizing and sustained-release ingredient; heavy mineral oil has known properties as an emollient, lubricant, and oleaginous vehicle making the wax softer and less rigid; polyethylene glycol-1500 (PEG 1500) enhances matrix hydrophilicity; Tween 80 (Polysorbate 80) serves as a wetting/dispersing/suspending agent in lipophilic bases; and xanthum gum is a stabilizing agent and suspending agent, as described in the Handbook of Pharmaceutical Excipients (7$^{th}$ Edition, London: Pharmaceutical Press, 2012), the relevant sections of which are expressly incorporated by reference herein in their entirety.

The following Instruments were used in evaluations: Mettler AE 200 weighing balance, 4802 UV/Vis double beam spectrophotometer, and Hanson Vision Elite 8 dissolution apparatus Microcrystalline wax was melted in a beaker placed in a water bath maintained at 90° C. Once melted, glyceryl monostearate was added, followed by 250 µL heavy mineral oil with mechanical stirring. At about the same time, PEG 1500 was melted in another beaker placed in a water bath maintained at 90° C. and stirred using a magnetic stirrer at 80 rpm. Benzocaine was added in portions every 2.5 min over a period of 12.5 min waiting for each addition to solubilize before adding the next. Tween 80 was added with continuous stirring and heat. Xanthum gum was then added in 0.25 g quantities over a period of two min while increasing stirring to 150 rpm. The wax mixture was poured into the PEG-drug mixture over two to three min while stirring at 200 rpm and stirred for an additional five min. The two mixtures were stirred mechanically with visual inspection. As soon as the wax began to solidify, the mixture was poured in a mold.

The formulation of Table 1A was assessed for an in vitro benzocaine release profile from the wax using an artificial saliva formulation that was prepared according to Table 2.

TABLE 2

Artificial saliva formulation

| Components | Quantity (mM) |
|---|---|
| $KH_2PO_4$ | 2.5 |
| $Na_2HPO_4$ | 2.4 |
| $KHCO_3$ | 15 |
| NaCl | 10 |
| $MgCl_2$ | 1.5 |
| $CaCl_2$ | 1.5 |
| citric acid | 0.15 | pH adjusted to 6.7 with dilute HCl

The in vitro analgesic/anesthetic release study used the artificial saliva formulation containing potassium phosphate monobasic ($KH_2PO_4$), sodium phosphate dibasic ($Na_2HPO_4$), potassium bicarbonate ($KHCO_3$), sodium chloride (NaCl), magnesium chloride hexahydrate ($MgCl_2 \cdot 6H_2O$), calcium chloride ($CaCl_2$), citric acid anhydrous, dilute hydrochloric acid (NCl), methanol, and MilliQ filtered water (resistivity=18.0 megaohms). Each ingredient was dissolved in 150-200 mL MilliQ filtered water and poured in a 4 L volumetric flask placed on a stirrer (350 RPM). $KH_2PO_4$, $Na_2HPO_4$ and $MgCl_2$ were ground before weighing. The final pH of the solution was adjusted to 6.7 using dilute HCl.

A standard curve of benzocaine was prepared. One mg benzocaine was dissolved in 20 mL methanol to make a stock solution. The stock solution was used to make 5 mL of increasing concentrations of benzocaine in artificial saliva (5 µM, 10 µM, 15 µM, 20 µM, 25 µM, 30 µM, 35 µM, 40 µM, 45 µM, 50 µM, 55 µM, and 60 µM). Absorbance of each concentration was measured at 284 nm using a UV/Vis double beam spectrophotometer. The cuvette was washed 3-4 times with water between each measurement. Each measurement was performed in triplicate, with the average absorbance of each concentration used to generate the standard curve.

A Hanson Vision Elite 8 dissolution apparatus was used for the in vitro benzocaine release study. Degassed artificial saliva was the dissolution medium (900 mL). The paddle speed was 50 rpm and the water bath was maintained at 37° C. Five mL of medium was withdrawn at each time point (0 min, 30 min, 60 min, 120 min, 180 min, 240 min, 300 min, 360 min, 420 min, 480 min, and 77 hours) and replaced by an equal volume of warm artificial saliva. Sinkers were used to place about 150 mg benzocaine wax in each basket.

The results of a standard benzocaine curve prepared in artificial saliva are reported in Table 3 and shown in FIG. 1.

TABLE 3

Standard absorbance curve for benzocaine in artificial saliva formulation

| Conc (µM) | Conc (µM) | Conc (µM) | Avg Conc of Benzocaine (µM) | Absorbance | Absorbance | Absorbance | Avg Absorbance at 284 nm |
|---|---|---|---|---|---|---|---|
| 1.05 | 1.02 | 1.05 | 1.04 | 0.018 | 0.011 | 0.013 | 0.014 |
| 2.55 | 2.48 | 2.55 | 2.53 | 0.051 | 0.04 | 0.048 | 0.046 |
| 5.23 | 5.08 | 5.23 | 5.18 | 0.101 | 0.08 | 0.097 | 0.093 |
| 10.33 | 10.04 | 10.33 | 10.23 | 0.206 | 0.159 | 0.19 | 0.185 |
| 15.43 | 15.00 | 15.43 | 15.29 | 0.325 | 0.243 | 0.307 | 0.292 |
| 20.59 | 20.02 | 20.59 | 20.40 | 0.421 | 0.314 | 0.407 | 0.381 |
| 25.69 | 24.98 | 25.69 | 25.46 | 0.528 | 0.396 | 0.479 | 0.468 |
| 30.79 | 29.94 | 30.79 | 30.51 | 0.616 | 0.489 | 0.577 | 0.561 |
| 35.83 | 34.83 | 35.83 | 35.50 | 0.740 | 0.585 | 0.724 | 0.683 |
| 40.99 | 39.85 | 40.99 | 40.61 | 0.849 | 0.684 | 0.816 | 0.783 |
| 46.03 | 44.75 | 46.03 | 45.60 | 0.921 | 0.708 | 0.91 | 0.846 |
| 51.06 | 49.64 | 51.06 | 50.59 | 1.105 | 0.833 | 1.021 | 0.986 |

Figure 2:
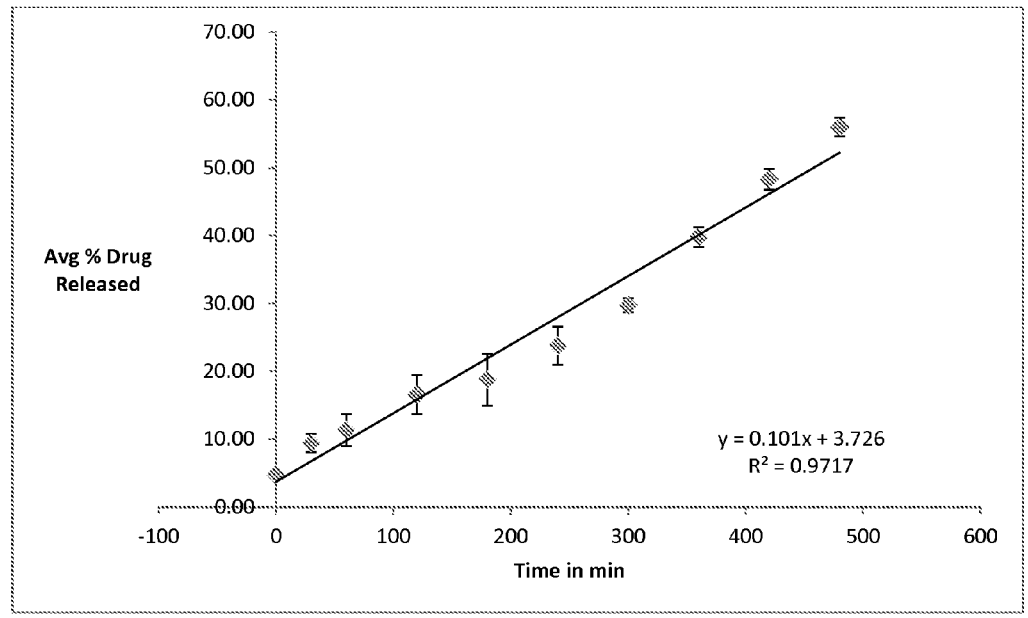
FIG. 2 illustrates the time release of benzocaine from an exemplary composition into an artificial saliva simulant, as determined by measurements using absorbance spectroscopy at 284 nm.

The results of in vitro release of 5% benzocaine, formulated as shown in Table 1A, in the artificial saliva formulation from Table 2 are reported in Table 4 and shown in FIG. 2.

TABLE 4

Time release profile of benzocaine into artificial saliva formulation

| Time (min) | % Drug Released | % Drug Released | % Drug Released | Avg % Drug Released | Std Deviation |
|---|---|---|---|---|---|
| 0 | 4.87 | 5.10 | 4.39 | 4.79 | 0.36 |
| 30 | 8.31 | 10.91 | 9.07 | 9.43 | 1.34 |
| 60 | 9.93 | 14.05 | 10.03 | 11.34 | 2.35 |
| 120 | 14.52 | 19.85 | 15.38 | 16.59 | 2.86 |
| 180 | 16.53 | 23.20 | 16.62 | 18.78 | 3.82 |
| 240 | 21.59 | 26.93 | 22.74 | 23.76 | 2.81 |
| 300 | 29.53 | 30.87 | 28.76 | 29.72 | 1.06 |
| 360 | 40.43 | 38.14 | 40.81 | 39.79 | 1.44 |
| 420 | 48.74 | 46.60 | 49.51 | 48.28 | 1.51 |
| 480 | 55.91 | 54.66 | 57.35 | 55.97 | 1.34 |

As the data show, this formulation had an average of 56% percent benzocaine released into the artificial saliva medium after eight hours. This release rate was more than twice that obtained for a previous first-generation formulation described in U.S. Pat. No. 6,074,674 (the '674 patent) which is expressly incorporated by reference herein in its entirety. The '674 patent formulation was 7.1% tragacanth, 70.9% microcrystalline wax, 2.0% Span 80, and 20.0% benzocaine. The '674 patent formulation had an in vitro release of only 22.7% benzocaine released into the medium after eight hours.

This difference was unexpected. Without being limited to a specific theory, and with all other variables being equal, Fick's Law of Diffusion would predict a greater release of analgesic/anesthetic agent from a matrix that contains a higher concentration of the analgesic/anesthetic agent. From the results shown herein, however, a greater percent of benzocaine was released from the disclosed formulation that contained a relatively lower benzocaine concentration, compared to that in the '674 patent. Specifically, the analgesic/anesthetic agent that was released from the formulation now disclosed was 11.3% at 1 hr, 16.6% at 2 hr, 18.8% at 3 hr, 23.8% at 4 hr, 29.7% at 5 hr, 39.8% at 6 hr, 48.3% at 7 hr, and 56.0% at 8 hr. The analgesic/anesthetic is released in one embodiment up to 24 h.

In embodiments using a sustained release agent, xanthum gum provided both a good release rate and a good product aesthetic appearance. Without being bound by a specific theory, this may be due to the structure of the xanthum gum compound, its hydrophilic characteristic, and its emulsifying property that may facilitate saliva penetration of the wax matrix and release of the analgesic/anesthetic. Xanthum gum is used in oral and topical pharmaceutical formulations, cosmetics, and foods as a suspending agent, stabilizing agent, thickening agent, and emulsifying agent. It is nontoxic, compatible with most other pharmaceutical ingredients, and has good stability and viscosity properties over a wide pH and temperature range. It has been used to prepare sustained-release matrix tablets. Such properties are known, as disclosed in the following references, each of which is expressly incorporated by reference herein in its entirety: Jansson P E, Kenne L, Lindberg B. Structure of extracellular polysaccharide from Xanthamonas campestris. Carbohydr Res 1975; 45: 275-282; Melton L D, Mindt L, Rees D A, Sanderson G R. Covalent structure of the polysaccharide from Xanthamonas campestris: evidence from partial hydrolysis studies. Carbohydr Res 1976; 46: 245-257; Dhopeshwarkar V, Zatz J L. Evaluation of xanthan gum in the preparation of sustained release matrix tablets. Drug Dev Ind Pharm 1993; 19: 999-1017.

Figure 3:
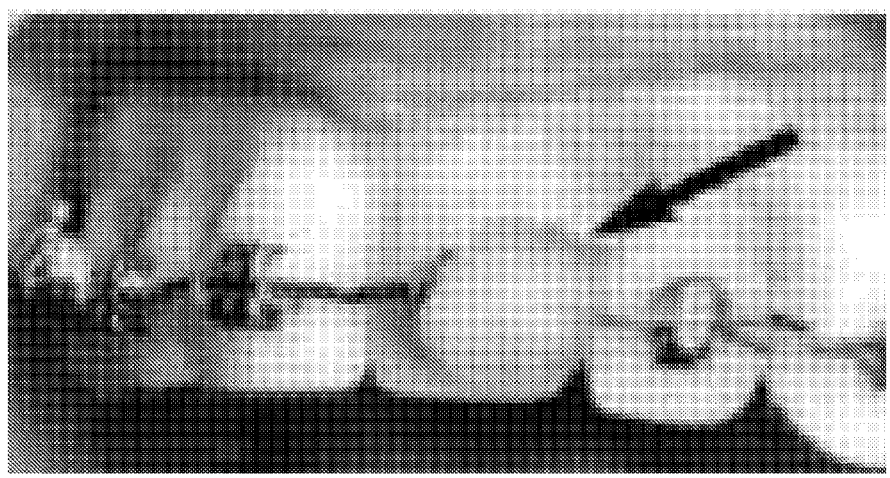
FIG. 3 illustrates an exemplary composition applied to an orthodontic bracket or brace affixed to a tooth of a patient.

Compared to the '674 patent formulation containing a relatively higher 15%-25% concentration of analgesic/anesthetic, the formulations disclosed herein have a lower concentration of analgesic/anesthetic agent. This results in enhanced patient safety and ease of regulatory approval, while also providing an enhanced release profile for increased efficacy. The formulations disclosed herein have an improved aesthetic appearance, facilitating patient use and compliance, and are more similar to unmedicated waxes, and less similar to the tragacanth-containing wax described in the '674 patent with a yellow appearance. The increased percentage of the wax matrix assists in retaining a wax-like character; sufficiently flexible to be broken off of a wax strip and applied to an orthodontic bracket without crumbling or falling apart, as shown in FIG. 3. This increases both patient acceptability, as well as formulation retention on orthodontic brackets. In use, the wax is applied to the bracket. It will then be in contact with the mucosa as the gums lay against the teeth. Without the wax, the mucosa lays against the metal bracket; this is the source of irritation to the mucosa. The wax will stay on the metal bracket because the wax is malleable. The wax will be molded onto the part of the bracket that protrudes and is in contact with the mucosa.

The ingredients that may be used in embodiments of the formulation are as follows:

Analgesic/anesthetic agents, also termed active agents, include benzocaine, lidocaine, novocaine, procaine, butalaine, dyclonine, prilocaine, tetracaine, butamben (butyl 4-aminobenzoate), cocaine, fidocaine, dibucaine, oxybuprocaine, pramoxine, proparacaine, proxymetacaine, amethocaine, cholorbutanol, ambroxol HCl, hexylresorcinol, amylmetacresol dichlorobenzylalcohol, dichlorobenzene, benzyl alcohol. Combinations of anesthetics include EMLA (eutectic mixture of local anesthetics) which is a combination of lidocaine and prilocaine; TAC which is a combination of tetracaine, adrenaline/epinephrine and cocaine; LET which is a combination of lidocaine, adrenaline/epinephrine and tetracaine.

A wax or mixture of waxes capable of serving as a matrix and maintaining its integrity after incorporation of all active ingredients and excipients, including after application in the mouth, may be used. Thus, any wax or combination of commercially available natural or synthetic waxes and including but not limited to the following may be used: anionic emulsifying wax, bleached wax, carnauba wax, cetyl esters wax, hard wax, microcrystalline wax, nonionic emulsifying wax, refined wax, white wax, white beeswax, yellow wax, yellow beeswax. In one embodiment, the wax is microcrystalline wax.

In one embodiment, a non-ionic polymer is selected from the group consisting of sodium carboxymethyl cellulose, CARBOPOL® ETD 2001 resin, tragacanth, poly(ethylene oxide), methylcellulose, hydroxy-propylmethylcellulose, karya gum, cellulose, soluble starch, gelatin, poly(vinyl pyrrolidone), poly (ethylene glycol) 8000, poly(ethylene glycol) 4000, poly(vinyl alcohol), and combinations thereof. In one embodiment, the non-ionic polymer is PEG 1500.

In one embodiment, the surfactant is selected from the group consisting of sorbitan monolaurate, polysorbate 80, Spans, Tweens, and combinations thereof. In one embodiment, the surfactant is polysorbate 80 (Tween 80).

In one embodiment, the formulation contains one or more swelling agents, emulsifiers, surfactants, and/or wetting agents, each described in the Handbook of Pharmaceutical Excipients. These may be included to optimize or otherwise alter the release of active, e.g., benzocaine, from the wax matrix, e.g., alginic acid (also known as E400, KELACID™, L-gulo-D-mannoglycuronan, polymannuronic acid, PROTACID®, SATIALGINE H8®); bentonite (also known as ABAGEL®, E558, MAGNABRITE®, mineral soap, POLARGEL®, soap clay, taylorite, VEEGUM® HS, wilkinite); calcium alginate (also known as alginic acid calcium salt, Algin, CA33, calc align, calcium polymannuronate, Calginate, E404, KALTOSTAT®); carbomer (also known as ACRITAMER®, acrylic acid polymer, CARBOPOL®, carboxy polymethylene, polyacrylic acid, carboxyvinyl polymer, PEMULEN®, CARBOPOL® Ultrez); carboxymethylcellulose calcium (also known as calcium carboxymethylcellulose, calcium CMC, ECG 505, NYMCEL® ZSC); carboxymethylcellulose sodium (also known as AKUCELL®, AQUASORB®, BLANOSE®, cellulose gum; CMC sodium); cellulose acetate phthalate (also known as acetyl phthalyl cellulose, AQUACOAT® cPD, CAP, cellacephate, cellulose acetate benzene-1,2-dicarboxylate, cellulose acetate hydrogen 1,2-benzenedicarboxylate, cellulose acetate hydrogen phthalate, cellulose acetate monophthalate, cellulose acetophthalate, cellulose acetylphthalate); *Ceratonia* (also known as Algaroba, carob bean gum, carob flour, *ceratonia* gum, *ceratonia siliqua, ceratonia siliqua* gum, Cheshire gum, E410, gomme de caroube, locust bean gum, Meyprofleur, St. John's bread); croscarmellose sodium (also known as AC-DI-SOL™ crosslinked carboxymethylcellulose sodium, EXPLOCEL™, modified cellulose gum, NYMCEL® ZSX, PHARMACEL® XL, PRIMELLOSE®, SOLUTAB®, VIVASOL®); crospovidone (also known as crosslinked povidone, E1202, KOLLIDON® CL, KOLLIDON® CL-M, POLYPLASDONE® XL, POLYPLASDONE® XL-10, polyvinylpolypyrrolidone, PVPP, 1-vinyl-2-pyrrolidinone homopolymer); gelatin (also known as BYCO™, CRYOGEL®, gelatin, INSTAGEL™, SOLUGEL™); glyceryl monooleate (also known as ALDO® MO, ATLAS™ G-695, CAPMUL® GMO, glycerol-1-oleate, glyceryl mono-oleate, KESSCO™ GMO, Ligalub, monolein, MONOMULS® 90-018, mono-olein, a-mono-olein glycerol, PECEOL®, PRIOLUBE® 1408, STEPAN® GMO, TEGIN®); guar gum (also known as E412, GALACTOSOL™, guar flour, jaguar gum, Meyprogat, MEYPRODOR™, Meyprofin); hectorite (also known as Hector clay, HECTABRITE® AW, HECTABRITE® DP, Ghassoulite, LAPONITE®, SHCa-1, Strese & Hofmann's Hectorite); hydroxyethyl cellulose (also known as CELLOSIZE® HEC, cellulose hydroxyethyl ether, cellulose hydroxyethylate, ethylhydroxy cellulose, ethylose, HEC, HE cellulose, 2-hydroxyethyl cellulose ether, hydroxyethyl ether cellulose, hydroxyethyl starch, hyetellose, NATROSOL®, oxycellulose, Tylose PHA); hypromellose (also known as BENECEL® MHPC, E464, hydroxypropyl methylcellulose, HPMC, METHOCEL®, methylcellulose propylene glycol ether, methyl hydroxypropylcellulose, METOLOSE®, TYLOPUR™); hypromellose acetate succinate (also known as AQOAT®, AQOAT® AS-HF/HG, AQOAT® AS-LF/LG, AQOAT® AS-MF/MG, cellulose 2-hydroxypropyl methyl ether acetate succinate, HPMCAS); hypromellose phthalate (also known as cellulose phthalate hydroxypropyl methyl ether, HPMCP, hydroxypropyl methylcellulose benzene-1,2-dicarboxylate, 2-hydroxypropyl methylcellulose phthalate, methylhydroxypropylcellulose phthalate); kaolin (also known as Argilla, bolus alba, China clay, E559, kaolinite, Lion, porcelain clay, Sim 90, weisserton, white bole); magnesium aluminum silicate (also known as aluminosilicic acid magnesium salt, aluminum magnesium silicate, Carrisorb, GELSORB™ MAGNABRITE®, magnesium aluminosilicate, magnesium aluminum silicate colloidal, magnesium aluminum silicate complex colloidal, NEUSILIN®, Pharmsorb, silicic acid aluminum magnesium salt, Veegum); methylcellulose (also known as BENECEL®, CULMINAL® MC, E461, METHOCEL®, METOLOSE®); polacrilin potassium (also known as AMBERLITE™ IRP-88, methacrylic acid polymer with divinylbenzene potassium salt, polacrilinum kalii); polycarbophil (also known as NOVEON® AA-1); polyethylene oxide (also known as POLYOX®, polyoxirane, polyoxyethylene); polymethacrylates (also known as ACRYL-EZE®, ACRYL-EZE® MP, EASTACRYL® 30D, EUDRAGIT®, KOLLICOAT® MAE 30 D, KOLLICOAT® MAE 30 DP, polymeric methacrylates; USP/NF non-proprietary names are Ammonio methacrylate copolymer, methacrylic acid copolymer, methacrylic acid copolymer dispersion; saponite (also known as Afrodit, aluminum-saponite, auxite, cathkinite, ferroan saponite, griffithite, licianite, lucianite); sodium starch glycolate (also known as carboxymethyl starch sodium salt, EXPLOSOL®, EXPLOTAB®, GLYCOLYS®, PRIMOJEL®, starch carboxymethyl ether sodium salt, TABLO™, VIVASTAR® P); starch (also known as Amido, amidon, amilo, amylum, AYTEX® P, C*PHARMGEL®, FLUFTEX™ W, INSTANT PURE-COTE®, MELOJEL®, Meritena, PAYGEL® 55, PERFECTAMYL® D6PH, PURE-BIND®, PURE-COTE®, PURE-DENT®, PURE-GEL®, PURE-SET®, Purity 21, Purity 826, Tablet White); tragacanth (also known as Algaroba, carob bean gum, carob flour, *ceratonia* gum, *ceratonia siliqua, ceratonia siliqua* gum, Cheshire gum, E410, gomme de caroube, locust bean gum, Meyprofleur, St. John's bread); xanthan gum (also known as corn sugar gum, E415, KELTROL®, polysaccharide B-1459, RHODIGEL®, VANZAN® NF, XANTURAL®); D-a-tocopherol (Vitamin E) (also known as COPHEROL® F1300, ( )-3,4-dihydro-2,5,7, 8-tetramethyl-2-(4,8,12-trimethyltridecyl)-2H-1-benzopyran-6-ol; E307, EASTMAN® Vitamin E TPGS, synthetic alpha tocopherol, all-rac-atocopherol, dl-a-tocopherol, 5,7,8-trimethyltocol); benzalkonium chloride (also known as alkylbenzyldimethylammonium chloride, alkyl dimethyl benzyl ammonium chloride, BKC, HYAMINE® 3500, Pentonium, ZEPHIRAN®); cetostearyl alcohol (also known as cetearyl alcohol, CRODACOL™ CS90, LANETTE® O, TEGO® Alkanol 1618, Tego Alkanol 6855); cetrimide (also known as BROMAT™, Cetab, CETAVLON®, Cetraol, Lissolamine V, Micol, Morpan CHSA, Morphans, Quammonium, Suticide); cetylpyridinium chloride (also known as C16-alkylpyridinium chloride, CEPACOL®, Cepacol chloride, Cetamiun, cetyl pyridium chloride, Dobendan, hexadecylpyridinium chloride, 1-hexadecylpyridinium chloride, Medilave, Pristacin; Pyrisept); diethanolamine (also known as bis(hydroxyethyl)amine, DEA, diethylolamine, 2,20-dihydroxydiethylamine, diolamine, 2,20-iminodiethanol); docusate sodium (also known as bis(2-ethylhexyl) sodium sulfosuccinate, dioctyl sodium sulfosuccinate, DSS, sodium dioctyl sulfosuccinate, sulfo-butanedioic acid 1,4-bis(2-ethylhexyl) ester sodium salt); glyceryl monostearate (also known as CAPMUL® GMS-50, CUTINA® GMS, 2,3-dihydroxypropyl octadecanoate, glycerine monostearate, glycerin monostearate, glycerol monostearate, glycerol stearate, glyceryl stearate, GMS, IMWITOR® 191, IMWITOR® 900, KESSCO™ GMS, Lipo GMS 410, Lipo GMS 450, Lipo GMS 600, monoester with 1,2,3-propanetriol, monostearin, MYVAPLEX™ 600P, MYVATEX™, 1,2,3-propanetriol octadecanoate, Protachem GMS-450, Rita GMS, stearic acid monoester with glycerol, stearic monoglyceride, STEPAN® GMS, TEGIN®, TEGIN® 503, TEGIN® 515, TEGIN® 4100, TEGIN® M, UNIMATE™ GMS); lauric acid (also known as C-1297, dodecanoic acid, dodecoic acid, duodecylic acid, n-dodecanoic acid, HYDROFOL™ acid 1255, HYDROFOL™ acid 1295, HYSTRENE® 9512, laurostearic acid, Neo-fat 12, Neo-fat 12-43, NINOL® AA62 Extra, 1-undecanecarboxylic acid, vulvic acid, Wecoline 1295); lecithin (also known as E322, egg lecithin, LSC 5050, LSC 6040, mixed soybean phosphatides, ovolecithin, PHOSAL® 53 MCT, PHOSPHOLIPON® 100 H, soybean lecithin, soybean phospholipids, Sternpur, vegetable lecithin); Macrogol 15 hydroxystearate (also known as 12-hydroxyoctadecanoic acid polymer with alpha-hydro-hydroxypoly(oxy-1,2-ethanediyl), polyethylene glycol 660 12-hydroxystearate, SOLUTOL® HS 15); medium-chain triglycerides (also known as BERGABEST®, caprylic/capric triglyceride, CAPTEX® 300, CAPTEX® 355, CRODAMOL™ GTC/C, glyceryl tricaprylate/caprate, LABRAFAC™ CC, MCT oil, MIGLYOL® 810, MIGLYOL® 812, MYRITOL®, NEOBEE® M5, Nesatol, oleum neutral, oleum vegetable tenue, thin vegetable oil, Waglinol 3/9280); monoethanolamine (also known as Δ-aminoethyl alcohol, colamine, ethylolamine, β-hydroxyethylamine, 2-hydroxyethylamine); myristic acid and its salts (also known as EDENOR® C14 98-100, n-tetradecanoic acid, 1-tridecanecarboxylic acid); palmitic acid and its salts (also known as cetylic acid, EDENOR® C16 98-100, EMERSOL® 140, EMERSOL® 143, n-hexadecoic acid, hexadecylic acid, HYDROFOL™, HYSTRENE® 9016, INDUSTRENE® 4516, 1-pentadecanecarboxylic acid, hexadecanoic acid sodium salt, palmitic acid sodium salt, sodium hexadecanoate, myricyl palmitate); Poloxamer (also known as Lutrol, MONOLAN™, PLURONIC®, poloxalkol, polyethylene-propylene glycol copolymer, polyoxyethylene-polyoxypropylene copolymer, Supronic, SYNPERONIC®); polyoxyethylene alkyl ethers (synonyms applicable to polyoxyethylene alkyl ethers are BRIJ®, CREMOPHOR® A, CYCLOGOL™ 1000, EMPILAN® KB, EMPILAN® KM, EMULGENT®, ETHYLAN™ C, macrogol ethers, MARLOWET®, PLURAFAC™, PROCOL®, Ritoleth, Ritox, Texofor A, Volpo); polyoxyethylene castor oil derivatives (also known as ACCONON®, ARLATONE®, CREMOPHOR®, ETOCAS™, EUMULGIN®, JEECHEM®, LIPOCOL®, MAPEG®, MARLOWET®, NIKKOL®, Protachem, SIMULSOL™; polyoxyethylene sorbitan fatty acid esters (also known as Tweens, polysorbates of varying molecular weight); polyoxyethylene stearates (also known as ethoxylated fatty acid esters, macrogol stearates, MARLOSOL™, PEG fatty acid esters, PEG stearates, polyethylene glycol stearates, poly (oxy-1,2-ethanediyl) a-hydro-o-hydroxyoctadecanoate, polyoxyethylene glycol stearates); potassium sorbate (also known as E202, 2,4-hexadienoic acid (E,E)-potassium salt, potassium (E,E)-hexa-2,4-dienoate, potassium (E,E)-sorbate; sorbic acid potassium salt); sodium lauryl sulfate (also known as dodecyl sodium sulfate, ELFAN® 240, sodium dodecyl sulfate, sodium laurilsulfate, sodium monododecyl sulfate, sodium monolauryl sulfate, TEXAPON® K12P); sorbitan esters (sorbitan fatty acid esters) (also known as Spans); stearic acid and its salts (also known as cetylacetic acid, crodacid, E570, EDENOR®, EMERSOL®, HYSTRENE®, INDUSTRENE®, KORTACID™ 1895, Pearl Steric, PRISTERENE®, stereophonic acid, Tegostearic); triethanolamine (also known as TEA, Tealan, triethylolamine, trihydroxytriethylamine, tris (hydroxyethyl)amine); triethyl citrate (also known as citric acid ethyl ester, CITROFLEX® 2, CITROFOL™ Al, E1505, HYDAGEN® CAT, TEC).

The embodiments shown and described in the specification are only specific embodiments of the inventor who is skilled in the art and thus are not limiting in any way. Various changes, modifications, or alterations may be made or resorted to without departing from the spirit of the invention or the scope of the following claims. As only two examples, additional actives may be incorporated into the formulation to provide additional medicinal effects, and/or the formulation may be provided in another type of carrier for self-application to the orthodontic bracket.

What is claimed is:

1. A method of alleviating orthodontic discomfort in a patient in need thereof, the method comprising applying a pharmaceutically acceptable composition of a wax, from 0.01% to less than 15% of an analgesic/anesthetic agent, and up to 30% xanthum gum to provide to the patient under conditions to alleviate orthodontic discomfort for at least eight hours and up to 24 hours after the application.

2. A method of alleviating orthodontic discomfort in a patient in need thereof, the method comprising applying a pharmaceutically acceptable composition of wax, glyceryl monostearate, heavy mineral oil, PEG 1500, Tween 80, from 0.01% to less than 15% of an analgesic/anesthetic agent, and up to 30% xanthum gum.

3. A method of alleviating orthodontic discomfort in a patient in need thereof, the method comprising applying a pharmaceutically acceptable composition of 83% microcrystalline wax, 2.7% glyceryl monostearate, 1.0% heavy mineral oil, 5% PEG 1500, 5% analgesic/anesthetic agent, 0.3% Tween 80, and 3% xanthum gum, the composition applied to an oral mucosal surface of the orthodontic patient under conditions to alleviate the orthodontic discomfort.

4. A method of alleviating orthodontic discomfort in a patient in need thereof, the method comprising applying a pharmaceutically acceptable composition of 50%-99% microcrystalline wax, 0%-10% glyceryl monostearate, 0%-30% heavy mineral oil, 0%-30% PEG 1500, 0.01%-14.99% analgesic/anesthetic agent, 0%-10% Tween 80, and 0.1%-30% xanthum gum, the composition applied to an orthodontic bracket or brace of the orthodontic patient under conditions to alleviate orthodontic discomfort.

5. The method of claim 1, the composition comprising from 50%-99% microcrystalline wax.

6. The method of claim 1, the composition comprising 83% microcrystalline wax.

7. The method of claim 1, the composition further comprising up to 10% glyceryl monostearate.

8. The method of claim 1, the composition further comprising up to 30% heavy mineral oil.

9. The method of claim 1, the composition further comprising up to 30% PEG 1500.

10. The method of claim 1, the composition further comprising up to 10% Tween 80.

11. The method of claim 1, the composition comprising 5% analgesic/anesthetic agent.

12. The method of claim 1, wherein the analgesic/anesthetic agent is benzocaine.

13. The method of claim 1, wherein the applying step applies the composition to an orthodontic bracket or brace affixed to at least one tooth of a patient.

14. The method of claim 1, wherein the applying step applies the composition to an oral mucosal surface in a patient.

15. A extended release pharmaceutically acceptable composition comprising microcrystalline wax, glyceryl monostearate, heavy mineral oil, PEG 1500, Tween 80, less than 15.0% of an analgesic/anesthetic agent, and up to 30% xanthum gum, the composition having an in-vitro release of the analgesic/anesthetic agent of about 28% to about 56% over eight hours.

16. The composition of claim 15, the composition comprising from 50%-99% microcrystalline wax.

17. The composition of claim 15, the composition further comprising up to 10% glyceryl monostearate.

18. The composition of claim 15, the composition further comprising up to 30% heavy mineral oil.

19. The composition of claim 15, the composition further comprising up to 30% PEG 1500.

20. The composition of claim 15, the composition further comprising up to 10% Tween 80.

21. The composition of claim 15, the composition comprising 5% analgesic/anesthetic agent.

22. The composition of claim 15, wherein the analgesic/anesthetic agent is benzocaine.

* * * * *